United States Patent
Oiwa

(10) Patent No.: US 11,446,414 B2
(45) Date of Patent: Sep. 20, 2022

(54) MEDICAL DEVICE

(71) Applicant: TERUMO KABUSHIKI KAISHA, Tokyo (JP)

(72) Inventor: Tomoya Oiwa, Fujinomiya (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 497 days.

(21) Appl. No.: 16/575,864

(22) Filed: Sep. 19, 2019

(65) Prior Publication Data

US 2020/0009300 A1 Jan. 9, 2020

Related U.S. Application Data

(63) Continuation of application No. PCT/JP2018/012151, filed on Mar. 26, 2018.

(30) Foreign Application Priority Data

Mar. 30, 2017 (JP) .............................. JP2017-067872

(51) Int. Cl.
*A61L 31/10* (2006.01)
*A61L 31/12* (2006.01)
(Continued)

(52) U.S. Cl.
CPC .............. *A61L 31/128* (2013.01); *A61L 31/10* (2013.01); *A61M 25/09* (2013.01);
(Continued)

(58) Field of Classification Search
CPC ............................... A61M 25/00; A61M 25/09
See application file for complete search history.

(56) References Cited

U.S. PATENT DOCUMENTS 7,695,753 B2 * 4/2010 Pursley ................ B05D 3/0209
427/421.1
2009/0312745 A1 * 12/2009 Goldfarb ................ A61B 17/24
604/514
(Continued)

FOREIGN PATENT DOCUMENTS

| CN | 101618249 A | 1/2010 |
| JP | 2010011883 A | 1/2010 |

(Continued)

OTHER PUBLICATIONS

Zhang et al. "Coatings and Coating Techniques", Chemical Industry Press, (Jan. 31, 2006) pp. 181-189 (Year: 2006).*

(Continued)

*Primary Examiner* — Cachet I Proctor
(74) *Attorney, Agent, or Firm* — Buchanan Ingersoll & Rooney PC

(57) ABSTRACT

The disclosed medical device has high visibility on non-woven fabric having a color such as green, blue, or the like, excellent identifiability from other medical devices having a color such as green, blue, or the like, and high surface smoothness. The medical device comprises an elongated body and a resin layer for covering at least a proximal portion of the elongated body, in which the resin layer has a first layer which includes a first fluororesin, titanium oxide, and a dispersant, and a second layer which is formed on the first layer and includes a second fluororesin. The content of the titanium oxide is 30% by weight or more relative to the solid content of the first layer, and an acid value of the dispersant is 20 to 90 mg/KOH.

23 Claims, 2 Drawing Sheets

(51) Int. Cl.
  *A61M 25/09*  (2006.01)
  *B05D 1/18*  (2006.01)
  *B05D 3/02*  (2006.01)
  *B05D 7/20*  (2006.01)
  *B05D 7/24*  (2006.01)
  *B05D 7/00*  (2006.01)

(52) U.S. Cl.
  CPC ....... *A61L 2420/02* (2013.01); *A61L 2420/04* (2013.01); *A61L 2420/08* (2013.01); *A61M 2025/09133* (2013.01); *B05D 1/18* (2013.01); *B05D 3/0254* (2013.01); *B05D 7/20* (2013.01); *B05D 7/24* (2013.01); *B05D 7/544* (2013.01)

(56) References Cited

U.S. PATENT DOCUMENTS

| | | | | |
|---|---|---|---|---|
| 2010/0004561 | A1* | 1/2010 | Nabeshima | A61M 25/09 600/585 |
| 2017/0303891 | A1* | 10/2017 | Yamashita | B29C 48/0018 |
| 2018/0207399 | A1* | 7/2018 | Chou | A61M 25/09 |
| 2020/0023101 | A1 | 1/2020 | Oiwa | |

FOREIGN PATENT DOCUMENTS

| | | | |
|---|---|---|---|
| JP | 2015100664 A | * | 6/2015 |
| JP | 2015100664 A | | 6/2015 |

OTHER PUBLICATIONS

BYK DISPERBYK-110—Product Data , Palmer Holland technical datasheet, Oct. 2012 (Year: 2012).*

BYK "Anti-TERRA-204". BYK additives & Instruments. Sep. 2012. byk.com/additives (Year: 2012).*

Zhang et al., "Coating and Printing Technology," Chemical Industry Press, (Jan. 31, 2006), pp. 181-189. (with an English Translation) (22 total pages).

Office Action (The first Office Action) dated Jun. 21, 2021, by the State Intellectual Property Office of People's Republic of China in corresponding Chinese Patent Application No. 201880020129.5 and an English Translation of the Office Action. (15 pages).

Office Action (Hearing Notice) dated Sep. 2, 2021, by the Patent Office, Government of India, in corresponding India Patent Application No. 201917038003 with an English Translation of the Office Action. (2 pages).

U.S. Appl. No. 16/575,570, filed Sep. 19, 2019, Oiwa.

BYK USA Inc., DISPERBYK-110, Palmer Holland Technical Data Sheet, [online], Oct. 2012, [search date Jun. 8, 2018], Retrieved from the internet: <URL:https://www.palmerholland.com/Assets/User/Documents/Product/41865/4344/MITM02613.pdf> in particular, "Recommended Use".

International Search Report (PCT/ISA/210) and translation and Written Opinion (PCT/ISA/237) dated Jun. 26, 2018, by the Japanese Patent Office as the International Searching Authority for International Application No. PCT/JP2018/012151.

Technical Information L-WI 1. Wetting dispersant, [online], pp. 1-16, Dec. 21, 2015, [search date Jun. 8, 2018], Retrieved from the internet: <URL:https://www.tetsutani.co.jp/wp-content/uploads/2015/12/21.pdf> (BYK Japan KK, Tetsutani & Co., Ltd. technical data).

The extended European Search Report dated Dec. 4, 2020, by the European Patent Office in corresponding European Patent Application No. 18776401.4-1109. (6 pages).

Office Action (Notice of Reasons for Refusal) dated Nov. 24, 2021, by the Japanese Patent Office in corresponding Japanese Patent Application No. 2019-509809 and an English Translation of the Office Action. (8 pages).

Lehtinen, "Paper Pigment Coating and Surface Sizing", China Light Industry Press, 1st Edition, (Mar. 31, 2005), with English Translation, pp. 219-220. (7 pages total).

Office Action (The Second Office Action) dated Nov. 10, 2021, by the State Intellectual Property Office of People's Republic of China in corresponding Chinese Patent Application No. 201880020129.5 and an English Translation of the Office Action. (17 pages).

Office Action (Examination Report) dated Aug. 14, 2020, by the Intellectual Property India in corresponding India Patent Application No. 201917038003 and an English Translation of the Office Action. (5 pages).

* cited by examiner

MEDICAL DEVICE

CROSS-REFERENCES TO RELATED APPLICATIONS

This application is a continuation of International Application No. PCT/JP2018/012151 filed on Mar. 26, 2018, and claims priority to Japanese Patent Application No. 2017-067872 filed on Mar. 30, 2017, the entire content of both of which is incorporated herein by reference.

FIELD OF THE INVENTION

The present invention generally relates to a medical device and method for fabricating or producing a medical device.

BACKGROUND DISCUSSION

A guide wire is a medical device which is employed for guiding a catheter used for percutaneous transluminal coronary angioplasty (PTCA), cardiovascular imaging test, or the like for treatment of a stenosis in coronary artery of heart. As a part of percutaneous transluminal coronary angioplasty, the guide wire is inserted in combination with a balloon catheter, in a state in which the guide wire protrudes beyond the distal end of the balloon catheter, to the vicinity of a stenosis in coronary artery as a target site. In the stenosis, only the thin guide wire passes through first to widen the stenosis, thus guiding the balloon catheter.

For the purpose of having easy movement in blood vessel or easy passage through a lesion or the like and also enhancing the sliding property to reduce the resistance with an inner wall of a catheter, it is typical for the guide wire that a resin layer such as fluororesin or the like is coated around a core member such as alloy or the like.

Accordingly, a medical device such as catheter, guide wire, or the like that is inserted to a lumen of a living body like airway, respiratory tract, gastrointestinal tract, urinary tract, blood vessel, or the like or a tissue is required to have an operability which enables clear insertion to a target site without damaging a tissue. Furthermore, the medical device is also required to exhibit an excellent sliding property so as to avoid a damage on mucosal membrane caused by friction or an occurrence of inflammation while the medical device is held in a tissue.

Meanwhile, since the medical device to be inserted to a lumen or a tissue of a living body has a small diameter, it may be sometimes difficult to immediately visually recognize the medical device in an operating room. As such, according to Japanese Application Publication No. 2015-100664, the visibility of a guide wire is increased by having green inorganic pigments such as chromium oxide, cobalt green, or the like contained in a resin layer to impart coloration to the guide wire.

SUMMARY

In an operating room in which percutaneous transluminal coronary angioplasty or the like is performed, non-woven fabric like surgical drape, cover for an instrument table, a gown, or the like is used. The color of the non-woven fabric is either green or blue in most cases. If a medical device has a color hue which belongs to the same color group as the non-woven fabric, the medical device and background color would have the same color so that there may be a case in which a doctor has a difficulty visually recognizing the medical device immediately. Accordingly, the guide wire should have various colors without being limited to green or blue described above.

Furthermore, for percutaneous transluminal coronary angioplasty, plural guide wires may be used simultaneously depending on the type of a lesion, a bending property, or the like. For a procedure in which plural medical devices are used simultaneously, it is preferable that a doctor can identify each medical device by a handle part. For a guide wire, a method for identifying each guide wire by forming a marker near a proximal portion of a guide wire is known. However, due to the long length of a guide wire, the handle part for a doctor is quite apart from the proximal portion of a guide wire so that a work involved in confirming the marker at the proximal portion of a guide wire would be burdensome to a doctor. Accordingly, to identify each medical device by a handle part, the guide wire is required to have various colors within a range in which the handle part for a doctor is included.

To enhance the visibility and identifiability of a medical device by a doctor, the medical device is preferably colored with a color such as red or the like that has high visibility and can be identified relative to or against green or blue. For example, for a guide wire, a method of coloring a guide wire with white by forming a coating containing fluororesin layer, which is blended with titanium oxide representing white, on an outer surface of a core member (elongated body) of a guide wire may be considered. The fluororesin layer on an outer surface of the core member (elongated body) of the guide wire is generally formed by baking after coating the coating solution having a fluororesin dispersed in a solvent on the core member.

However, when titanium oxide is blended in large amounts in the coating solution for the purpose of imparting coloration, there may be a case in which aggregates of titanium oxide are generated in large amounts and precipitated in the coating solution so that a sufficient amount of titanium oxide is not coated on the core member. Furthermore, even in a case in which the core member can be coated with a coating solution, irregularities are generated on a surface of the coating due to the aggregates of titanium oxide and the surface smoothness of a medical device is impaired in some cases.

The medical device disclosed here has high visibility on or against non-woven fabric with green, blue, or the like, excellent identifiability or distinguishability from other medical devices having colors such as green, blue, or the like, and exhibits high surface smoothness.

One aspect of the disclosure here involves a medical device comprises an elongated body and a resin layer for covering at least a proximal portion of the elongated body, in which the resin layer has a first layer which includes a first fluororesin, titanium oxide, and a dispersant and a second layer which is formed on the first layer and includes a second fluororesin, the content of the titanium oxide is 30% by weight or more relative to the solid content of the first layer, and an acid value of the dispersant is 20 to 90 mgKOH/g.

According to another aspect, a medical device comprises: an elongated body possessing a distal-most end, a proximal-most end and a distal portion extending from the distal-most end of the elongated body towards the proximal-most end of the elongated body; a first resin layer covering the proximal portion of the elongated body and not covering the distal portion of the elongated body, with the first resin layer having a composition that includes a first fluororesin, titanium oxide, and a polymer dispersant that facilitates dispersion of the titanium oxide in the first fluororesin; and a second resin layer covering the first resin layer and not covering the distal portion of the elongated body, with the second resin layer having a composition that includes a second fluororesin. The content of the titanium oxide in the first resin layer is 30% by weight or more relative to a solid content of the first layer to color so that the proximal part of the medical device is colored, is visible against a colored fabric used in an operating room and is identifiable from other medical devices that are colored. The polymer dispersant possesses an acid value that is 20 to 90 mgKOH/g to inhibit reduction of dispersion of the titanium oxide in the first fluororesin and avoid negatively impacting surface smoothness of the proximal part of the medical device.

In accordance with another disclosed aspect, a method comprises coating a first coating solution on at least a proximal portion of an elongated body to form a first coating film on the proximal portion of the elongated body, wherein the first coating solution that is coated on the proximal portion of the elongated body to form the first coating film includes a first fluororesin, titanium oxide, and a dispersant having an acid value of 20 to 90 mgKOH/g; coating a second coating solution on the first coating film to form a second coating film, wherein the second coating solution that is coated on the first coating film to form the second coating film includes a second fluororesin; and baking the elongated body coated with the first and second coating films at a temperature which is equal to or higher than a melting point of the first fluororesin and a melting point of the second fluororesin.

DETAILED DESCRIPTION

Figure 1:
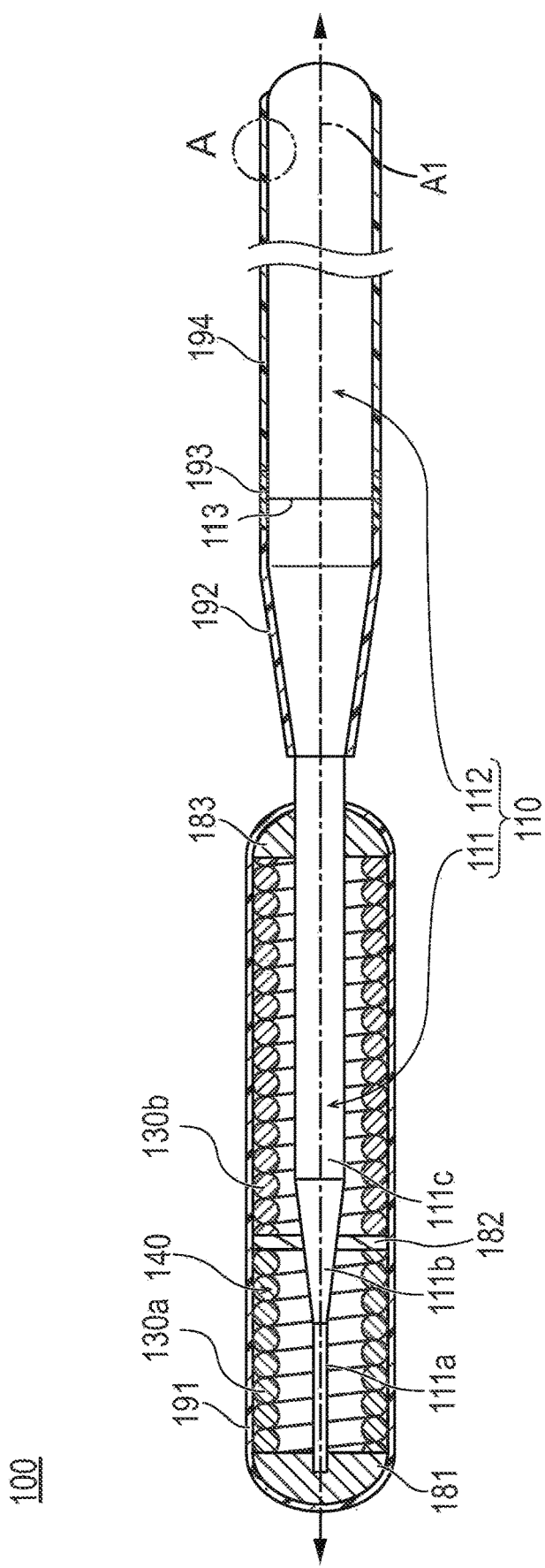
FIG. 1 is a partial longitudinal cross-sectional view illustrating a guide wire 100 (cross-sectional view along the axial direction of guide wire 100).

Generally speaking, one embodiment of a medical device according to the disclosure here may comprise an elongated body and a resin layer for covering at least a proximal portion of the elongated body, in which the resin layer has a first layer which includes a first fluororesin, titanium oxide, and a dispersant and a second layer which is formed on the first layer and includes a second fluororesin, the content of the titanium oxide is 30% by weight or more relative to the solid content of the first layer, and an acid value of the dispersant is 20 to 90 mgKOH/g.

By using a specific dispersant which has a favorable adsorption property to titanium oxide and favorable compatibility with a fluororesin and a solvent, aggregates are not generated in a coating solution even for a system in which titanium oxide is blended in large amounts, and also coating with high surface smoothness is obtained. The medical device having this coating becomes a medical device which exhibits high visibility on non-woven fabric with green, blue, or the like (i.e., the medical device is quite visible against non-woven fabric colored green, blue, or the like), excellent identifiability (distinguishability) from other medical devices having a color such as green, blue, or the like (i.e., the medical device is quite distinguishable from other medical devices colored green, blue, or the like), and high surface smoothness.

Hereinbelow, embodiments of the medical device representing examples of the inventive medical device disclosed here are described. The present invention is not limited to the following embodiments.

In the present specification, the expression "X to Y" indicating a range includes X and Y and means "X or more and Y or less". Furthermore, in the present specification, unless particularly described otherwise, operations and measurements of physical properties and the like are performed under conditions at room temperature (20° C. or higher and 25° C. or lower) and relative humidity (RH) of 40% RH or more and 50% RH or less.

The medical device according to the present embodiment is a medical device that is used after insertion into a living body, for example, and, specifically, examples of the medical device include catheters such as an indwelling needle, an IVH catheter, a thermo-dilution catheter, an angiographic catheter, a dilatation catheter (for example, a PTCA catheter), a dilator, an introducer, and the like which are inserted into or caused to indwell in a blood vessel, or a guide wire and a stylet for these catheters; catheters such as a gastric tube catheter, a nutritional catheter, a tube for tube-feeding nutrition (ED), and the like which are orally or nasally inserted into or caused to indwell in a digestive organ; catheters such as an oxygen catheter, an oxygen cannula, a tube or a cuff of an endotracheal tube, a tube or a cuff of a tracheotomy tube, an endotracheal suction catheter, and the like which are orally or nasally inserted into or caused to indwell in the airway or the trachea; catheters such as a urethral catheter, a catheter for guiding urine, a catheter or a balloon of a urethral balloon catheter, and the like which are inserted into or caused to indwell in the urethra or the ureter; catheters such as a suction catheter, a drainage catheter, a rectum catheter, and the like which are inserted into or are caused to indwell in various types of body cavities, internal organs, and tissues; an artificial trachea and an artificial bronchus; medical devices (an artificial lung, an artificial heart, an artificial kidney, and the like) for extracorporeal circulation treatment or circuits thereof; medical devices such as an endoscope which is inserted into various types of organs and is required to have low frictional resistance with respect to the outer surface and the like of a living body when being inserted into, being caused to slide into, and being caused to indwell in the living body; and the like.

Among them, the medical device is preferably a catheter or a guide wire, and is particularly preferably a guide wire.

The description below describes an example in which the medical device is a guide wire such as shown in FIG. 1. The dimensional ratio of the drawings is exaggerated for the sake of convenience for description, and it may be different from the actual ratio.

FIG. 1 is a partial longitudinal cross-sectional view illustrating the guide wire 100 (cross-sectional view along the axial direction of guide wire 100).

As illustrated in FIG. 1, the guide wire 100 has an elongated core portion (core wire) 110 having flexibility, a wire member 140 wound in a spiral shape so that the wound wire member 140 is in surrounding but spaced relation to a part of the core wire 110. The wound wire member 140 is comprised of a first coil portion 130a and a second coil portion 130b that are disposed so cover at least the distal portion of the core portion 110. That is, the distal portion of the core portion 110 and the wound wire member 140 (the first and second coil portions 130a, 130b) axially overlap one another. Furthermore, as illustrated in FIG. 1, on an outer surface of the guide wire 100, resin layers 191, 192, 193, and 194 to be described later are formed in this order from the distal end side. Furthermore, the illustration of the resin layer does not necessarily indicate an embodiment in which the aforementioned four resin layers 191, 192, 193, 194 are adjacent to each other, and other resin layers or an exposed portion of the core wire having no resin layer may be included between each axially adjacent resin layer. Furthermore, the medical device is not necessarily limited to an embodiment in which the aforementioned four resin layers are necessarily provided, and at least one layer of the resin layers 191, 192, and 193 may not be included (i.e., at least one of the resin layers 191, 192, 193 may be excluded). Furthermore, it is possible to increase the resin layer(s), for example, each resin layer may be formed of two or more resin layers in which each layer is different from each other.

In the following description, the length direction of the core portion 110 (left and right direction in FIG. 1) is defined as the axial direction, and it is identified by the arrow A1 in each drawing. Furthermore, the side or end of the guide wire 100 which is introduced into a living body (into a blood vessel) is defined as a distal end side or distal end (distal side, left side of FIG. 1), and the end or side opposite to the distal end side is defined as a proximal end side or proximal end (proximal side, right side of FIG. 1). Furthermore, the distal portion described in the present specification means a portion which includes a certain range in the axial direction from the distal end (distal-most end), while the proximal portion means a portion which includes a certain range in axial direction from the proximal end (proximal-most end). In that case, the proximal portion does not necessarily include the proximal end (proximal-most end).

The core portion 110 is an elongated body having a first elongated core portion 111 disposed on the distal end side in the axial direction and a second elongated core portion 112 disposed on the proximal end side of the first core portion 111 and bonded (fixed) to the first core portion 111. The total length of the core portion 110 may preferably be 500 to 5000 mm, though is not limited in this regard. In particular, the core portion 110 of a guide wire used for PTCA generally has total length of 1700 to 3000 mm.

The first elongated core portion 111 has an elongated flat plate-shaped flat plate portion 111a which is disposed on the distal end side of the first core portion, an elongated tapered portion 111b which extends from the flat plate portion 111a toward the proximal end side, and an elongated constant outer diameter portion 111c which extends, at roughly constant outer diameter, from the tapered portion 111b toward the proximal end side. As shown in FIG. 1, in the illustrated embodiment, the tapered portion 111b extends immediately from the proximal-most end of the flat plate portion 111a, and the constant outer diameter portion 111c extends immediately from the proximal-most end of the tapered portion 111b. Furthermore, the shape of the first core portion 111 is not limited to the illustrated shape. The first core portion 111 may be also formed to have a constant outer shape (constant outer diameter) from the distal end side toward the proximal end side, for example. Furthermore, it is also possible that the core portion 110 is not constituted by plural members like the first core portion 111 and the second core portion 112. Instead, the core portion 110 may be constituted by a single continuous member, for example. As for the width and thickness of the flat plate portion 111a, the width may be 0.1 to 0.5 mm or so and the thickness may be 0.01 to 0.1 mm or so, for example. Furthermore, the outer diameter of the constant outer diameter portion 111c may be 0.2 to 1 mm or so, for example.

Materials for constituting the first core portion 111 and the second core portion 112 are not particularly limited, but various metal materials such as Ni—Ti based alloy, stainless steel such as SUS302, SUS304, SUS303, SUS316, SUS316L, SUS316J1, SUS316J1L, SUS405, SUS430, SUS434, SUS444, SUS429, SUS430F or the like, a piano wire, a cobalt-based alloy, and super-elastic alloy or the like can be used for each, for example. Among them, the material for constituting the first core portion 111 is preferably Ni—Ti based alloy, and the material for constituting the second core portion 112 is preferably stainless steel. The material for constituting the second core portion 112 may be the same or different from the material constituting the first core portion 111. The first core portion 111 and the second core portion 112 may be bonded by a bonding portion or fixing portion 113 according to a method that includes welding or the like, for example.

A first coil portion 130a and a second coil portion 130b (hereinbelow, they are also collectively referred to as a coil portion 130) are disposed so as to cover, or surround within a certain range in the axial direction, the first core portion 111. The coil portion 130 is constituted by the wire member 140 which is wound in spiral shape along the peripheral direction of the core portion 110 while having the core portion 110 (the first core portion 111) at the center.

The wire member 140 has an approximately cylindrical shape with a lumen (i.e., the wound wire member 140 surrounds a lumen) to accommodate the first core portion 111.

The inner diameter and outer diameter of the coil portion 130 are constant, inclusive of substantially constant, along the axial direction. Furthermore, the length of the coil portion 130 in the axial direction, as well as the outer diameter and the inner diameter of the coil portion 130, are not particularly limited, and they can be suitably set depending on the product specification or the like of the guide wire 100.

The first coil portion 130a is fixed, via a first fixing portion 181 and a second fixing portion 182, on the periphery of the flat plate portion 111a and the tapered portion 111b of the first core portion 111, respectively. The second coil portion 130b is fixed, via the second fixing portion 182 and a third fixing portion 183, on the periphery of the tapered portion 111b and the constant outer diameter portion 111c of the first core portion 111, respectively. Each of the fixing portion 181, 182, and 183 may be constituted by solder, brazing material, adhesive, or the like. In consideration of an influence on a lumen of a living body such as blood vessel or the like, the distal end surface of the first fixing portion 181 preferably has a rounded shape as illustrated. The second fixing portion 182 is located at the tapered portion 111b of the first core portion 111.

The material for constituting the wire member 140 to form the coil portion 130 is not particularly limited, and stainless steel, super-elastic alloy, cobalt-based alloy, metal such as gold, platinum, tungsten, or the like, or alloys containing these materials, and the like can be used. It is also possible that, for the coil portion 130, the distal portion and proximal portion thereof are constituted of different materials, for example. For example, the first coil portion 130a may be formed of a material having a radio-opaque property (for example, platinum), or the like, while the second coil portion 130b may be formed of a material which transmits X-rays more easily compared to the distal portion (for example, stainless steel). FIG. 1 shows that the cross-section of a wire member in the coil portion 130 has a round shape, but the wire member forming the coil portion 130 may also possess an elliptical cross-section, a rectangular cross-section, or the like.

As illustrated in FIG. 1, the resin layer 191 is formed on the outer surface of the first coil portion 130a and on the outer surface of the second coil portion 130b. The resin layer 191 may be formed for various purposes. For example, it may be formed for the purpose of enhancing the safety at the time of inserting the guide wire 100 into a blood vessel or the like. For this purpose, the resin layer 191 is preferably hydrophilic. Examples of the hydrophilic material for constituting the resin layer 191 include a cellulose-based polymer material, a polyethylene oxide-based polymer material, a maleic anhydride-based polymer material (for example, a maleic anhydride copolymer such as methyl vinyl ether-maleic anhydride copolymer), an acrylamide-based polymer material (for example, polyacrylamide, block copolymer of polyglycidyl methacrylate-dimethyl acrylamide (PGMA-DMAA)), water-soluble nylon, polyvinyl alcohol, polyvinyl pyrrolidone, or the like. In most cases, those hydrophilic materials exhibit a high lubricating property when wetted (water absorption). Because the distal portion is required to have a high lubricating property, it is preferable to use those hydrophilic materials for the distal portion. The thickness of the resin layer 191 is suitably set depending on the purpose, material, or the like, but the average thickness at wetting is 0.1 to 300 μm, for example.

Furthermore, on the outer surface of the proximal end side of the first core portion 111, the resin layer 192 is formed. The resin layer 192 may be a material capable of reducing friction. Examples of the material capable of reducing friction include polyolefin such as polyethylene, polypropylene or the like, polyvinyl chloride, polyester (PET, PBT, or the like), polyamide, polyimide, polyurethane, polystyrene, polycarbonate, a silicone resin, a fluorine-based resin (PTFE, ETFE, or the like), and composite materials thereof. Furthermore, the resin layer 192 may also include a component other than the material capable of reducing friction (for example, organic pigment), and it may have the same constitution as the resin layer 194 to be described later, for example. Namely, according to one embodiment, the resin layer 192 has a first layer which includes a first fluororesin, titanium oxide, and a dispersant and a second layer which is formed on the first layer and includes a second fluororesin, and the content of the titanium oxide is 30% by weight or more relative to the solid content of the first layer and an acid value of the dispersant is 20 to 90 mgKOH/g. By virtue of this composition, the resin layer 192 may be also colored.

As illustrated in FIG. 1, the resin layer 193 is formed on the outer surface of the core portion including the bonding portion 113 of the first core portion 111 and the second core portion 112. The resin layer 193 preferably exhibits a sliding property. Examples of a material for the resin layer 193 include polyolefin such as polyethylene, polypropylene, or the like, polyvinyl chloride, polyester (PET, PBT, or the like), polyamide, polyimide, polyurethane, polystyrene, polycarbonate, a silicone resin, a fluorine-based resin (PTFE, ETFE, or the like), composite materials thereof, or the like.

At least part of the second core portion 112 is coated with the resin layer 194. Namely, the resin layer 194 is a resin layer which covers at least the proximal portion of the elongated body. To provide a medical device with visibility and identifiability, the resin layer 194 is constituted by or comprised of a first layer (first resin layer) which includes a first fluororesin, titanium oxide, and a dispersant and a second layer (second resin layer) which is formed on the first layer and includes a second fluororesin. In addition, with regard to the resin layer 194, the content of the titanium oxide in the first layer is 30% by weight or more relative to the solid content of the first layer and an acid value of the dispersant is 20 to 90 mgKOH/g.

The resin layer 194 is preferably formed in a range including a handle part for a doctor. That is, the resin layer 194 is preferably provided on a part of the guide wire 100 (medical device) that includes a part gripped by the doctor during use. The expression "range including a handle part for a doctor" includes, in the case of a guiding catheter having a length that is common for percutaneous transluminal coronary angioplasty (length of 800 to 1000 mm), a portion of the guide wire that is exposed from the catheter proximal end. Specifically, an example includes an embodiment in which the resin layer 194 is formed between a position which is separated by 300 mm from the distal end (i.e., distal-most end) of a guide wire toward the proximal end side and the proximal end of the guide wire. Furthermore, the expression the resin layer 194 "is formed between a position which is separated by 300 mm from the distal end of a guide wire toward the proximal end side and the proximal end of a guide wire" means that the resin layer 194 may be formed over the total length (continuously) of the core portion 110 between the position that is spaced 300 mm from the distal end (i.e., distal-most end) toward the proximal end side and the proximal end of the guide wire, or the resin layer 194 may be formed on a part of the core portion 110 between the position that is spaced 300 mm from the distal end toward the proximal end side and the proximal end of the guide wire. According to the embodiment in which the resin layer 194 is formed on a part of the core portion 110 between a position which is separated by 300 mm from the distal end toward the proximal end side and the proximal end of a guide wire, it is possible to have not only an embodiment in which the resin layer 194 is continuously formed on such part but also an embodiment in which the resin layer 194 is formed at plural separate sites on such part. Thus, the resin layer 194 may extend continuously along the entire axial extent of the core portion 110 from a point spaced 300 mm in the proximal direction from the distal-most end of the guide wire to the proximal end of the core portion 110, or the resin layer 194 may extend along only a part of the axial extent of the core portion 110 from a point spaced 300 mm in the proximal direction from the distal-most end of the guide wire to the proximal end of the core portion 110. In the case of the resin layer 194 extending along only a part of such axial extent of the core portion 110, the resin layer 194 may extend continuously along such part of the axial extent or may extend as plural spaced part segments along such part of the axial extent.

According to an embodiment in which the resin layer 194 "is formed between the position that is separated by 300 mm from the distal end of a guide wire toward the proximal end side and the proximal end of a guide wire", it is preferable that the resin layer 194 is formed between the position that is separated by 300 mm from the distal end (i.e., distal-most end) of a guide wire toward the proximal end side and the position that is separated by 3500 mm from the distal end of the guide wire toward the proximal end side (Embodiment 1). It is more preferable that the resin layer 194 is formed between the position that is separated by 300 mm from the distal end (i.e., distal-most end) of a guide wire toward the proximal end side and the position that is separated by 3000 mm from the distal end of the guide wire toward the proximal end side. It is even more preferable that the resin layer 194 is formed between the position that is separated by 350 mm from the distal end (i.e., distal-most end) of a guide wire toward the proximal end side and the position that is separated by 3000 mm from the distal end (i.e., distal-most end) of the guide wire toward the proximal end side. As the resin layer 194 is formed in the aforementioned range, the guide wire can have a colored range in a handle part used by the doctor to operate the guide wire. Due to this reason, for a procedure involving simultaneous use of plural medical devices, a doctor can rather easily identify each medical device by a handle part even without checking a marker on a proximal end of the guide wire. Furthermore, according to an embodiment in which the resin layer 194 "is formed between the position that is separated by 300 mm from the distal end of a guide wire toward the proximal end side and the proximal end of a guide wire", the resin layer 194 may be formed on the proximal end side of a guide wire. Specifically, the resin layer 194 may be provided at least on a part of the region between the position that is separated by 50 mm from the proximal end (i.e., proximal-most end) of a guide wire toward the distal end side and the proximal end of a guide wire (Embodiment 2). With the resin layer 194 formed in the aforementioned range, easy identification of a guide wire can be achieved at the time of catheter exchange made by a doctor. The guide wire disclosed here may be embody Embodiment 1, may embody Embodiment 2, or may embody both Embodiment 1 and Embodiment 2.

As for the embodiment in which the resin layer 194 is formed on a part of a guide wire between the position that is separated by or spaced 300 mm from the distal end (i.e., distal-most end) of a guide wire toward the proximal end side and the proximal end of a guide wire, when the total length of a guide wire is 1800 mm, for example, (1) the resin layer 194 may be formed at least on a part between the position that is separated by or spaced 400 mm from the distal end (i.e., distal-most end) of a guide wire toward the proximal end side and the position that is separated by or spaced 1500 mm from the distal end (i.e., distal-most end) of a guide wire toward the proximal end side, and/or (2) the resin layer 194 may be formed at least on a part between the position that is separated by or spaced 1750 mm from the distal end or spaced of a guide wire toward the proximal end side and the position that is separated by or spaced 1790 mm from the distal end (i.e., distal-most end) of a guide wire toward the proximal end side. By forming the resin layer 194 on the part (1) above, easier identification of a guide wire by a handle part can be achieved by a doctor, and, by forming the resin layer 194 on the part (2) above, easy identification of a guide wire can be achieved at the time of catheter exchange made by a doctor.

Figure 2:
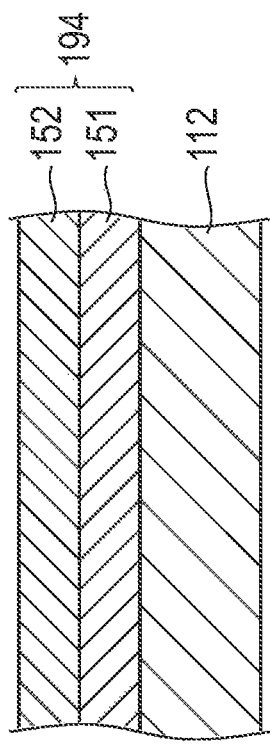
FIG. 2 is an enlarged sectional view of an area [II] surrounded by a one-dot chain line in FIG. 1.

FIG. 2 is an enlarged sectional view of an area [II] surrounded by a one-dot chain line in FIG. 1. In FIG. 2, the resin layer 194 includes a first layer 151 and a second layer 152. In FIG. 2, a second core portion 112, the first layer 151, and the second layer 152 are disposed in this order. Namely, the first layer 151 is an inner layer and is disposed on a second core portion (elongated body) side, and the second layer 152 is an outermost layer disposed on the first inner layer 151. The distal-most end of each of first and second resin layers 151, 152 is proximal of the proximal-most end of the tapered portion 111*b* as shown in FIG. 1.

The second layer 152 includes a fluororesin (second fluororesin). The operation for inserting a guide wire involves a part of the proximal end side (proximal side) entering the inside of a catheter. As the second layer 152 includes a fluororesin, frictional resistance on the outer surface of the guide wire is reduced. As a result, frictional resistance (sliding resistance) between the guide wire and the inner wall of the catheter is reduced, and thus the operability of the guide wire inside the catheter is enhanced. In addition, as the second layer 152 includes a fluororesin, kinking (bending) or twisting of a guide wire can be inhibited or prevented when the guide wire is moved/rotated inside the catheter.

Furthermore, with regard to FIG. 1, since the proximal end (proximal-most end) of the guide wire is never introduced into a human body, the proximal end need not exhibit a lubricating property. Thus, considering the manner of use of the guide wire, the proximal end (proximal-most end) is not provided with the resin layer 194. Accordingly, the proximal portion described in the expression that a resin layer "covers at least a proximal portion of an elongated body" is not limited to an embodiment in which the entire proximal end is provided with the resin layer 194, and, it is sufficient that a certain region or a part on the proximal end side of the guide wire is coated with the resin layer.

The content of the titanium oxide in the second layer 152 is preferably less than 5% by weight (lower limit: 0% by weight), more preferably less than 3% by weight (lower limit: 0% by weight), even more preferably less than 1% by weight (lower limit: 0% by weight), and most preferably 0% by weight relative to the solid content of the second layer. As the content of the titanium oxide in the second layer is low, not only the surface smoothness of the second layer as an outermost layer is enhanced but also peeling of the second layer can be suppressed. Furthermore, the content of particles other than titanium oxide that are included in the second layer (for example, inorganic pigment or organic pigment other than that) is also preferably less than 5% by weight (lower limit: 0% by weight), more preferably less than 3% by weight (lower limit: 0% by weight), even more preferably less than 1% by weight (lower limit: 0% by weight), and most preferably 0% by weight. According to the most preferred embodiment, the second layer substantially does not include any particles. The expression "substantially does not include" allows inclusion of particles which are present at a level of impurities, and the particles are included at 0.01% by weight or less (lower limit: 0% by weight) relative to the solid content of the second layer, for example, and the content of the particles is suitably 0% by weight. Furthermore, the solid content means a component excluding a solvent which evaporates at the time of drying or calcining a coating solution, and, in general, the solid content corresponds to the total weight of constitutional components constituting the second layer such as fluororesin, organic pigment, titanium oxide, dispersant, thickening agent, or the like.

The second layer including a fluororesin to provide the sliding property has a very low adhesion property to an elongated body such as a core member or the like. To enhance the adhesion property between the second layer and an elongated body, the first layer is provided between an elongated body and the second layer. That is, the first layer is formed on or overlies an elongated body, and the second layer is formed on or overlies the first layer.

The expression "the second layer is formed on the first layer" indicates that an elongated body, the first layer, and the second layer are formed or arranged in this order, and it does not necessarily indicate an embodiment in which the second layer and the first layer are directly adjacent to each other. It is also possible that an intermediate layer is included between the first layer and the second layer.

Similarly, it is not necessary that the first layer and an elongated body are directly adjacent to each other, and it is possible that an intermediate layer is included between an elongated body and the first layer. However, for increasing the adhesion property of the second layer to the elongated body, it is preferable that the elongated body and the first layer are directly adjacent to each other and also the first layer and the second layer are directly adjacent to each other as illustrated in FIG. 2.

The first layer may be either a single layer or a multi-layer, and the second layer may be either a single layer or a multi-layer.

[Resin Layer]

The resin layer 194 includes the first layer 151 which includes a first fluororesin, titanium oxide, and a dispersant, and the second layer 152 which is formed on the first layer and includes a second fluororesin.

The thickness of the resin layer is not particularly limited. However, from the viewpoint of imparting sliding properties or from the viewpoint of imparting visibility or identifiability, the thickness of the resin layer 194 is preferably 1 µm or more, more preferably 2 µm or more, and even more preferably 3 µm or more. Furthermore, in consideration of the adhesion properties of the coating or the influence on physical properties of the guide wire, the thickness of the resin layer is preferably 200 µm or less, more preferably 100 µm or less, and even more preferably 50 µm or less. Specifically, the thickness of the resin layer is preferably 1 to 200 µm, and more preferably 3 to 50 µm.

The first layer 151 includes the first fluororesin and the second layer 152 includes the second fluororesin.

The first fluororesin and the second fluororesin are not particularly limited, but, from the viewpoint of imparting sliding properties to the surface, chemical resistance, anti-thrombogenicity, non-sticking property, or the like, they preferably contain at least one selected from the group consisting of polytetrafluoroethylene (PTFE), tetrafluoro-ethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE). They more preferably contain polytetrafluoroethylene (PTFE), and more preferably contain at least one of polytetrafluoroethylene (PTFE) and tetrafluoroethylene-hexafluoropropylene copolymer (FEP). From the viewpoint of melting the first layer and the second layer at even lower temperatures, it is particularly preferable for the first fluororesin to contain both of polytetrafluoroethylene (PTFE) and tetrafluoroethylene-hexafluoropropylene copolymer (FEP). In that case, the weight ratio between PTFE and FEP is preferably 1:0.1 to 1:15, more preferably 1:1 to 1:10, and even more preferably 1:1 to 1:7. Furthermore, it is particularly preferable that the second fluororesin is polytetrafluoroethylene (PTFE).

The first fluororesin and the second fluororesin may be the same type or a different type. Furthermore, it is also possible that each of the first fluororesin and the second fluororesin contains plural kinds of a fluororesin.

For enhancing the visibility or identifiability (distinguishability) of a medical device according to coloration of the first layer by titanium oxide, the content of the titanium oxide is 30% by weight or more relative to the solid content of the first layer. Furthermore, the content of the titanium oxide is preferably 40% by weight or more relative to the solid content of the first layer, and more preferably 50% by weight relative to the solid content of the first layer. With the content within this range, the medical device, or portion of the medical device, exhibits a white color and increased brightness, and the identifiability (distinguishability) of the medical device from an existing guide wire colored green or the like is enhanced as is the visibility of the medical device on non-woven fabric. From the viewpoint of enhancing the surface smoothness of a medical device or adhesion property of a coating, the content of the titanium oxide is preferably 75% by weight or less relative to the solid content of the first layer, and more preferably 60% by weight or less relative to the solid content of the first layer. Furthermore, from the viewpoint of the color-exhibition property and surface smoothness, the content is preferably 30 to 75% by weight relative to the solid content of the first layer, and more preferably 40 to 60% by weight relative to the solid content of the first layer. Furthermore, for the same reason, the content of the titanium oxide is preferably 60 to 250% by weight relative to the first fluororesin.

The titanium oxide may be any one of rutile type and anatase type. However, in terms of the color-exhibition property, the titanium oxide is preferably a rutile type.

The particle diameter of the titanium oxide is preferably 10 to 900 nm, and more preferably 90 to 600 nm from the viewpoint of the dispersion property. The particle diameter of the titanium oxide indicates a median diameter based on volume that is measured by a laser diffraction scattering method.

The first layer includes a dispersant, and, in the present embodiment, an acid value of the dispersant is 20 to 90 mgKOH/g. When the acid value is less than 20 mgKOH/g, the dispersion property of titanium oxide in a fluororesin may be excessively reduced and the surface smoothness of a coating may be significantly lowered (see, Comparative Examples 1 and 2 that are described later). Furthermore, when the acid value is more than 90 mgKOH/g, the dispersion property of titanium oxide in a fluororesin may also be excessively reduced and the surface smoothness of a coating may be lowered (see, Comparative Examples 3 and 4 that are described later). It is considered that, as a dispersant having an acid value of 20 to 90 mgKOH/g has a favorable adsorption property to titanium oxide and favorable compatibility with a fluororesin, the dispersion property of titanium oxide inside the fluororesin layer is enhanced. A dispersant having an acid value of less than 20 mgKOH/g may have a lower dispersion property of titanium oxide due to insufficient adsorption to the titanium oxide. On the other hand, a dispersant having an acid value of more than 90 mgKOH/g may cause excessive adsorption onto titanium oxide, and thus the compatibility with titanium oxide and a fluororesin may be reduced. As a result, it is considered that, with a dispersant which has an acid value outside the aforementioned range, the dispersion property of titanium oxide inside the fluororesin layer is reduced.

Hereinbelow, the dispersant having an acid value of 20 mgKOH/g or more and 90 mg/KOH or less is also referred to as dispersant A.

The acid value is defined as the milligram number (number of milligrams) of potassium hydroxide that is required for neutralizing an acid included in 1 g of solid content of a dispersant, and it is a value measured based on the potentiometric titration method described in JIS K 0070: 1992.

The acid value of the dispersant A is, from the viewpoint of the dispersion property of titanium oxide in the fluororesin layer, preferably 30 mgKOH/g or more, and more preferably 40 mgKOH/g or more. Similarly, from the viewpoint of the dispersion property of titanium oxide in the fluororesin layer, the acid value of the dispersant A is preferably 85 mgKOH/g or less, and more preferably 80 mgKOH/g or less. The acid value of the dispersant A is, from the viewpoint of further enhancing the dispersion property of titanium oxide in the fluororesin and further increasing the surface smoothness, preferably 40 to 85 mgKOH/g, and more preferably 40 to 70 mgKOH/g.

The amine value of the dispersant A is, from the viewpoint of having favorable balance between the acid value and amine value and further enhancing the dispersion property of titanium oxide in the fluororesin, preferably 0 mgKOH/g or more and 100 mgKOH/g or less, more preferably 30 mgKOH/g or more and 80 mgKOH/g or less, and even more preferably 30 mgKOH/g or more and 70 mgKOH/g or less. The amine value indicates the total amine value, and it is measured based ASTM D2074.

The dispersant A is preferably a polymer dispersant. Based on steric hindrance of a main chain or a side chain, the polymer dispersant suppresses aggregation among titanium oxides to have enhancement of the dispersion property and stabilization of titanium oxide. Weight average molecular weight of a polymer constituting the dispersant A is preferably 500 or more, more preferably 1,000 or more, and even more preferably 2,000 or more, and it is preferably 200,000 or less and more preferably 150,000 or less. As the weight average molecular weight is within the aforementioned range, the adsorption property of the dispersant to titanium oxide is further enhanced, and therefore desirable. Furthermore, weight average molecular weight of a polymer constituting the dispersant A indicates polystyrene-converted weight average molecular weight that is measured by gel permeation chromatography (solvent for development: tetrahydrofuran).

Examples of the polymer type dispersant include polyaminoamide-based dispersant such as polycarbonate salt of polyaminoamide, phosphate salt of polyaminoamide, polyester acid salt of polyaminoamide, or the like: polyester-based dispersant; polycarboxylic acid ester-based dispersant such as polyurethane, polyacrylate, or the like; and polycarboxylic acid (salt)-based dispersant such as polycarboxylic acid, polycarboxylic (partial) amine salt, polycarboxylic acid ammonium salt, polycarboxylic acid alkylamine salt, or the like.

As for the polymer type dispersant, a commercially available product may be used. Examples of the commercially available product which may be used include ANTI-TERRA series (manufactured by BYK-Chemie) such as ANTI-TERRA (registered trademark)-U (acid value: 24 mgKOH/g, amine value: 19 mgKOH/g, salt of unsaturated polyaminoamide and low molecular weight polyester acid), ANTI-TERRA (registered trademark)-U100 (acid value: 50 mgKOH/g, amine value: 35 mgKOH/g, salt of unsaturated polyaminoamide and low molecular weight polyester acid), ANTI-TERRA (registered trademark)-204 (acid value: 41 mgKOH/g, amine value: 37 mgKOH/g, polycarboxylic acid salt of polyaminoamide), or the like, AJISPER series (manufactured by Ajinomoto Fine-Techno Co., Inc.) such as AJISPER-PA111 (acid value: 35 mgKOH/g, high fatty acid ester), or the like, and DISPERBYK series (manufactured by BYK-Chemie) such as DISPERBYK (registered trademark)-110 (acid value: 53 mgKOH/g, amine value: 0 mgKOH/g), DISPERBYK (registered trademark)-118 (acid value: 36 mgKOH/g, amine value: 0 mgKOH/g), DISPERBYK (registered trademark)-140 (acid value: 73 mgKOH/g, amine value: 76 mgKOH/g), DISPERBYK (registered trademark)-142 (acid value: 46 mgKOH/g, amine value: 43 mgKOH/g), DISPERBYK (registered trademark)-145 (acid value: 76 mgKOH/g, amine value: 71 mgKOH/g) or the like, and the like.

Furthermore, the dispersant is preferably a solvent-based dispersant. The solvent-based dispersant indicates a dispersant which can be either dispersed or dissolved in any one of organic solvents at room temperature.

The dispersant is preferably a polyaminoamide-based dispersant, and it is more preferably a polycarboxylic acid salt of polyaminoamide. It is considered that, according to a dispersant having this structure, the nitrogen atom has an affinity for titanium oxide and a portion other than the nitrogen atom increases the affinity for a fluororesin, and thus the dispersion property of titanium oxide in the fluororesin is enhanced overall.

As for the polyaminoamide-based dispersant, a commercially available product may be used. Examples of the commercially available polyaminoamide-based dispersant which may be used include ANTI-TERRA series (manufactured by BYK-Chemie) such as ANTI-TERRA (registered trademark)-U100 (acid value: 50 mgKOH/g, amine value: 35 mgKOH/g, salt of unsaturated polyaminoamide and low molecular weight polyester acid), ANTI-TERRA (registered trademark)-U (acid value: 24 mgKOH/g, amine value: 19 mgKOH/g, salt of unsaturated polyaminoamide and low molecular weight polyester acid), ANTI-TERRA (registered trademark)-204 (acid value: 41 mgKOH/g, amine value: 37 mgKOH/g, polycarboxylic acid salt of polyaminoamide) or the like, and the like.

The blending amount of the dispersant A is, from the viewpoint of the dispersion property of titanium oxide and compatibility in the first fluororesin, 0.10 to 3.00% by weight, 0.10 to 2.00% by weight, 0.10 to 1.5% by weight, 0.15 to 1.00% by weight, 0.40 to 1.00% by weight, 0.40 to 0.80% by weight, 0.40 to 0.70% by weight in preferred order relative to the titanium oxide. With the addition amount of the dispersant A within the above range, the surface smoothness is enhanced and, simultaneously, due to a relatively small amount of the dispersant, a decrease in the adhesion property at an interface between the first layer and the second layer, which is caused by an addition of the dispersant, can be suppressed. Furthermore, the blending ratio of the dispersant A is obtained to the third decimal digit, and a value obtained by rounding to the second decimal digit is employed.

Only one kind of the dispersant A may be used, or two or more kinds of the dispersant may be used in combination.

Furthermore, to further enhance the dispersion stability of the titanium oxide or to control the coating thickness with adjustment of the viscosity of a coating solution for forming the first layer, it is preferable for the resin layer to further contain a thickening agent. It is more preferable that the first layer contains a thickening agent. Examples of the thickening agent include polyamide-based wax, metal soaps, organic clay mineral, polyethylene oxide-based compound, hydrogenated castor oil wax, and inorganic fine particles such as fine powder of silicon dioxide, or the like. From the viewpoint of further enhancing the stability of a coating solution, the thickening agent is more preferably metal soaps, organic clay mineral, polyethylene oxide-based compound, or inorganic fine particles such as fine powder of silicon dioxide or the like. From the viewpoint that the dispersion property of the titanium oxide is further stabilized, organic clay mineral is more preferable.

Examples of the organic clay mineral include a material obtained by performing organic treatment of a clay mineral such as natural mineral montmorillonite (bentonite), hectorite, saponite that are classified into smectites, layered clay mineral, chain-like clay mineral such as sepiolite or the like, and long-fiber shape clay mineral such as palygorskite or the like. The organic treatment is generally performed by using an alkyl quaternary ammonium compound, and, by hydrophobizing the surface of clay mineral, the dispersion property of the obtained organic clay mineral is enhanced.

As for the thickening agent, a commercially available product may be used. Examples of the thickening agent which may be used include BENTONE LT, BENAQUA 4000 (Elementis Specialties), Optigel CK, Optigel LX, GARAMITE 7305 (manufactured by BYK-Chemie), KUNIBIS (registered trademark)-110, SUMECTON (registered trademark)-SA, SUMECTON (registered trademark)-SAN, SUMECTON (registered trademark)-STN (manufactured by KUNIMINE INDUSTRIES CO., LTD.), S-BEN (registered trademark) N400, S-BEN (registered trademark) NX, S-BEN (registered trademark) NZ (manufactured by HOJUN Co., Ltd.), or the like.

The blending amount of the thickening agent is suitably set in consideration of the blending amount of the titanium oxide, dispersant to be used, or the like. From the viewpoint of the stability of a coating solution, the thickening agent is preferably 0.50 to 3.00% by weight relative to the solid content of the first layer, more preferably 0.50 to 2.50% by weight relative to the solid content of the first layer, even more preferably 0.75 to 2.00% by weight relative to the solid content of the first layer, and particularly preferably 0.80 to 1.85% by weight relative to the solid content of the first layer. Furthermore, the blending ratio of the thickening agent is obtained to the third decimal digit, and a value obtained by rounding to the second decimal digit is employed.

Only one kind of the thickening agent may be used, or two or more kinds of the thickening agent may be used in combination.

The first layer may also include a binder resin for the purpose of enhancing the adhesion property to an elongated body. The binder resin is not particularly limited, and examples thereof include a polyamideimide resin, an epoxy resin, a polyphenylene sulfide resin, a polyether sulfone resin, a polyether ketone resin, a polyether amide resin, a polysulfone resin, a polyimide resin, a parylene resin, or the like. Only one kind of the binder resin may be used, or two or more kinds of the binder resin may be used in combination.

The content of the binder resin in the first layer is, in consideration of the adhesion property to an elongated body, preferably 5 to 50% by weight relative to the solid content of the first layer, and more preferably 10 to 40% by weight relative to the solid content of the first layer.

The first layer may include particles other than titanium oxide (for example, pigment for coloration). However, if the content of the particles is excessively high, the first layer becomes brittle, yielding an insufficient effect of enhancing the adhesion property of the second layer to an elongated body. For this reason, the content of the particles other than titanium oxide is preferably 10% by weight or less (lower limit: 0% by weight), and more preferably 5% by weight or less (lower limit: 0% by weight).

The content of the first fluororesin in the first layer is, in consideration of the adhesion property to the second layer, preferably 5 to 50% by weight relative to the solid content of the first layer, and more preferably 10 to 40% by weight relative to the solid content of the first layer.

The thickness of the first layer is, although not particularly limited, from the viewpoint of the visibility and identifiability of the medical device, preferably 0.8 μm or more, more preferably 1 μm or more, and even more preferably 2 μm or more. Furthermore, the thickness of the first layer is, in consideration of the adhesion property between the first layer and a layer adjacent to the first layer (for example, elongated body, the second layer, an intermediate layer which is adjacent to the first layer, or the like), preferably 100 μm or less, more preferably 50 μm or less, even more preferably 25 μm or less, and particularly preferably 10 μm or less. Furthermore, the thickness of the first layer is preferably 0.8 to 100 μm, more preferably 1 to 50 μm, even more preferably 1 to 25 μm, and particularly preferably 2 to 10 μm.

The content of the second fluororesin in the second layer is, in consideration of the effect of exhibiting the sliding property of the surface of a medical device, preferably 75 to 100% by weight, and more preferably 85 to 100% by weight.

The thickness of the second layer is, in consideration of providing the sliding property to a medical device and suppressing discoloration of the first layer which is caused by baking, preferably 0.8 μm or more, more preferably 1 μm or more, and even more preferably 2 μm or more. Furthermore, in consideration of the adhesion property between the second layer and a layer adjacent to the second layer (for example, the first layer, an intermediate layer which is adjacent to the second layer, or the like), the thickness of the second layer is preferably 50 μm or less, more preferably 25 μm or less, and even more preferably 10 μm or less.

Furthermore, the thickness of a layer described in the present specification indicates an average thickness value which is obtained from the thickness of 5 points that are arbitrarily selected from a part in which the subject layer is present. Furthermore, the thickness of each layer can be measured from a cress-sectional image of a medical device. Specifically, after taking a cross-sectional image of a medical device, by taking half of the value that is obtained by subtracting the outer diameter of the elongated body from the outer diameter of the medical device, the thickness of a layer can be calculated. In that case, the thickness is obtained to the second decimal digit, and an average value obtained by rounding the second decimal digit to the first decimal digit is employed. The thickness of the first layer can be calculated by subtracting the thickness of the second layer from the total thickness of a coating (resin layer).

Each layer constituting the resin layer may be also added with other additives, if necessary. Examples of the additives include an organic pigment, an inorganic pigment, a dispersion stabilizer, a leveling agent, an anti-foaming agent, a chelating agent, an anti-oxidant, a plasticizer, or the like.

[Production Method]

With regard to the medical device of the present embodiment, although not particularly limited, a production method may include coating a coating solution including a first fluororesin, titanium oxide, and a dispersant having an acid value of 20 to 90 mgKOH/g (hereinbelow, referred to as a coating solution for forming the first layer) at least on a proximal portion of an elongated body to form a first coating film, coating a coating solution including a second fluororesin (hereinbelow, referred to as a coating solution for forming the second layer) on the first coating film to form a second coating film; and then carrying out baking at a temperature which is equal to or higher than the melting points of the first fluororesin and the second fluororesin.

First, the coating solution for forming the first layer is prepared. The coating solution for forming the first layer includes the first fluororesin, titanium oxide, the binder resin, and the dispersant. The coating solution preferably includes a solvent, which is a dispersion medium for dispersing them (i.e., for dispersing the first fluororesin, titanium oxide, the binder resin, and the dispersant). As for the solvent, water, an organic solvent, and a mixture solvent of water and organic solvent can be used.

As for the organic solvent, an aromatic solvent such as toluene, xylene or the like, a ketone-based solvent such as acetone, methyl ethyl ketone, methyl isobutyl ketone, cyclohexanone or the like, and a cellosolve-based organic solvent such as methyl cellosolve, ethyl cellosolve, or the like can be mentioned. Only one kind of the organic solvent may be used, or two or more kinds of the organic solvent may be used in combination.

The amount of the organic solvent that is added is suitably set in consideration of the viscosity of the coating solution and dispersion property of each component. However, preferably, the organic solvent is added such that it is present at 40 to 70% by weight in the coating solution for forming the first layer.

The order of mixing the organic solvent with each component is not particularly limited, and it may be any addition order like mixing in bulk the organic solvent and each component or adding each component in turn to the organic solvent, or the like.

The method for coating the coating solution for forming the first layer on a proximal portion of the elongated body is not particularly limited. Specifically, dipping (immersing), dripping, a doctor blade, spin coating, brush coating, spray coating, a roll coater, air knife coating, curtain coating, wire bar coating, gravure coating, screen printing, or the like can be mentioned. From the viewpoint of having an even coating on a surface and easily controlling the film thickness, dipping (immersing) is preferably used as the method for coating the coating solution for forming the first layer. The pulling-up speed for dipping is suitably set so as to have a desired film thickness. An example of a pulling-up speed is 5 to 150 mm/second. Furthermore, the viscosity of the coating solution is suitably set so as to have a desired film thickness. An example of the viscosity of the coating solution is 5 to 70 Pa·s (25° C.).

It is preferable that, after the coating solution for forming the first layer is coated at least on the proximal portion of the elongated body, the coating solution for forming the first layer is dried. The drying temperature is not particularly limited as long as it allows removal of a solvent. However, it is preferably 50 to 300° C., and more preferably 100 to 200° C. The drying time is not particularly limited, either, as long as it allows removal of a solvent. However, it is preferably 10 minutes or shorter, more preferably 5 minutes or shorter, and even more preferably 60 seconds or shorter.

Furthermore, it is also possible that the steps of coating and drying are repeated.

The first coating film is obtained as described above.

Subsequently, the coating solution for forming the second layer is prepared. The coating solution for forming the second layer includes the second fluororesin. The coating solution preferably includes a solvent, which is a dispersion medium for dispersing the second fluororesin. As for the solvent, water, an organic solvent, and a mixture solvent of water and organic solvent can be used. As for the organic solvent, an organic solvent used for the above coating solution for forming the first layer can be mentioned.

Prepared coating solution for forming the second layer is coated on the first coating film. The method for coating the coating solution for forming the second layer on the first coating film is not particularly limited. Specifically, dipping (immersing), dripping, a doctor blade, spin coating, brush coating, spray coating, a roll coater, air knife coating, curtain coating, wire bar coating, gravure coating, screen printing, or the like can be mentioned. From the viewpoint of having an even coating on a surface and easily controlling the film thickness, dipping (immersing) is preferably used as the method for coating the coating solution for forming the second layer. The pulling-up speed for dipping is suitably set so as to have a desired film thickness. An example of a pulling-up speed is 5 to 150 mm/second. Furthermore, the viscosity of the coating solution is suitably set so as to have a desired film thickness. An example of the viscosity of the coating solution is 5 to 70 Pa s (25° C.).

It is preferable that, after the coating solution for forming the second layer is coated on the first coating film, the coating solution for forming the second layer is dried. The drying temperature is not particularly limited as long as it allows removal of a solvent. However, it is preferably 50 to 300° C., and more preferably 100 to 200° C. The drying time is not particularly limited, either, as long as it allows removal of a solvent. However, it is preferably 10 minutes or shorter, more preferably 5 minutes or shorter, and even more preferably 60 seconds or shorter.

The second coating film is obtained as described above.

Finally, baking is carried out at a temperature which is equal to or higher than the melting points of the first fluororesin and the second fluororesin. By carrying out the baking at a temperature which is equal to or higher than the melting points, the fluororesins are melted to form a coating.

The baking temperature is not particularly limited as long as it is equal to or higher than melting points of the first fluororesin and the second fluororesin. The baking temperature is preferably higher, by 20° C. or more, than the higher one of the melting points of the first fluororesin and the second fluororesin (i.e., the baking temperature preferably exceeds, by at least 20° C., the greater of the melting point of the first fluororesin and the melting point of the second fluororesin). The baking temperature is preferably 300 to 550° C., and more preferably 400 to 550° C. The baking time is preferably 30 seconds or longer. By virtue of this baking time of 30 seconds or longer, baking of the fluororesins is suitably carried out, and thus enhanced adhesion property and strength are yielded. The upper limit of the baking time is, although not particularly limited, from the viewpoint of the production efficiency and reducing the coloration (yellowness), preferably 2 minutes or shorter, and more preferably 60 seconds or shorter.

EXAMPLES

Hereinbelow, the effect of the medical device disclosed here is described by using the following Examples and Comparative Examples. In the Examples, descriptions like "parts" and "%" are used, and, unless specifically described otherwise, they represent "parts by weight" and "% by weight", respectively. Furthermore, unless specifically described otherwise, each operation is carried out at room temperature (25° C.).

Example 1

(Preparation of Coating Solution for Forming the First Layer)

50 g of titanium oxide (C.I. Pigment white 6, rutile type, average particle diameter of 250 nm), 148.6 g of methyl isobutyl ketone as a solvent, 5.8 g of polytetrafluoroethylene (PTFE, average particle diameter of 0.20 μm, melting point of 327° C.), 17.6 g of tetrafluoroethylene-hexafluoropropylene copolymer (FEP, average particle diameter of 0.20 μm, melting point of 270° C.), 23.0 g of polyphenylene sulfide resin as a binder resin, 0.50 g of AJISPER-PA111 (manufactured by Ajinomoto Fine-Techno Co., Inc., acid value: 35 mgKOH/g, amine value: 0 mgKOH/g, polymer dispersant) as the dispersant A (relative to the titanium oxide: 1.00% by weight), and 1.0 g of GARAMITE 7305 (manufactured by BYK-Chemie) as a thickening agent (relative to the solid content: 1.02% by weight) were admixed with one another and stirred using a ball mill to prepare a coating solution for forming the first layer.

(Preparation of Coating Solution for Forming the Second Layer)

By mixing 100.0 g of polytetrafluoroethylene (PTFE, average particle diameter of 0.20 μm, melting point of 327° C.) with 100.0 g of water, a coating solution for forming the second layer was prepared.

A metal element wire (SUS302, outer diameter of 0.340 mm) was immersed in the coating solution for forming the first layer, and pulled up at 40 mm/second. After that, it was dried for 60 seconds at 200° C. by using a heater. Subsequently, the metal element wire coated with the first layer was immersed in the coating solution for forming the second layer, and pulled up at 20 mm/second. After that, the metal element wire coated with the first and second layers was dried for 60 seconds at 200° C. by using a heater. Finally, the metal element wire coated with the first and second layers was calcined for 60 seconds at 500° C. to obtain a guide wire.

The thickness of the first layer of the obtained guide wire was 2.0 μm, the thickness of the second layer was 3.0 μm, and the thickness of the resin layer (the first layer+the second layer) was 5.0 μm.

Example 2

A guide wire was obtained in the same manner as Example 1 except that, for preparing a coating solution for forming the first layer, 0.31 g of ANTI-TERRA-204 as the dispersant A (manufactured by BYK-Chemie, acid value: 41 mgKOH/g, amine value: 37 mgKOH/g, polymer dispersant) (relative to the titanium oxide: 0.62% by weight) is used instead of 0.50 g of AJISPER-PA111 (manufactured by Ajinomoto Fine-Techno Co., Inc., acid value: 35 mgKOH/g) as the dispersant A.

Example 3

A guide wire was obtained in the same manner as Example 1 except that, for preparing a coating solution for forming the first layer, 0.50 g of DISPERBYK (registered trademark)-145 as the dispersant A (manufactured by BYK-Chemie, acid value: 76 mgKOH/g, amine value: 71 mgKOH/g, polymer dispersant) (relative to the titanium oxide: 1.00% by weight) is used instead of 0.50 g of AJISPER-PA111 (manufactured by Ajinomoto Fine-Techno Co., Inc., acid value: 35 mgKOH/g) as the dispersant A.

Comparative Example 1

A guide wire was obtained in the same manner as Example 1 except that, for preparing a coating solution for forming the first layer, 0.50 g of DISPARLON DA-703-50 (manufactured by Kusumoto Chemicals, Ltd., acid value: 15 mgKOH/g, amine value: 40 mgKOH/g) (relative to the titanium oxide: 1.00% by weight) is used instead of 0.50 g of AJISPER-PA111 (manufactured by Ajinomoto Fine-Techno Co., Inc., acid value: 35 mgKOH/g) as the dispersant A.

Comparative Example 2

A guide wire was obtained in the same manner as Example 1 except that, for preparing a coating solution for forming the first layer, 0.50 g of AJISPER-PB881 (manufactured by Ajinomoto Fine-Techno Co., Inc., acid value: 17 mgKOH/g, amine value: 17 mgKOH/g) (relative to the titanium oxide: 1.00% by weight) is used instead of 0.50 g of AJISPER-PA111 (manufactured by Ajinomoto Fine-Techno Co., Inc., acid value: 35 mgKOH/g) as the dispersant A.

Comparative Example 3

A guide wire was obtained in the same manner as Example 1 except that, for preparing a coating solution for forming the first layer, 0.50 g of DISPERBYK (registered trademark)-180 (manufactured by BYK-Chemie, acid value: 94 mgKOH/g, amine value: 94 mgKOH/g) (relative to the titanium oxide: 1.00% by weight) is used instead of 0.50 g of AJISPER-PA111 (manufactured by Ajinomoto Fine-Techno Co., Inc., acid value: 35 mgKOH/g) as the dispersant A.

Comparative Example 4

A guide wire was obtained in the same manner as Example 1 except that, for preparing a coating solution for forming the first layer, 0.50 g of DISPERBYK (registered trademark)-102 (manufactured by BYK-Chemie, acid value: 101 mgKOH/g, amine value: 0 mgKOH/g) (relative to the titanium oxide: 1.00% by weight) is used instead of 0.50 g of AJISPER-PA111 (manufactured by Ajinomoto Fine-Techno Co., Inc., acid value: 35 mgKOH/g) as the dispersant A.

(Evaluation Method: Surface Smoothness)

Surface smoothness of the obtained guide wires was observed based on the following criteria.

5: Pigment aggregates are hardly observed on the coating surface either with a naked eye or using a microscope.

4: Pigment aggregates are hardly observed on the coating surface with a naked eye, but, according to the observation using a microscope, slight pigment aggregates are observed from a coating surface.

3: Slight pigment aggregates are observed on the coating surface with a naked eye, but it is not problematic in terms of actual use.

2: Pigment aggregates are observed on the coating surface with a naked eye to the extent that they are problematic in terms of actual use.

1: Many pigment aggregates are observed on the coating surface with a naked eye.

The results are shown in the following Table 1.

TABLE 1

| | Example 1 | Example 2 | Example 3 | Comparative Example 1 | Comparative Example 2 | Comparative Example 3 | Comparative Example 4 |
|---|---|---|---|---|---|---|---|
| Acid value (mgKOH/g) | 35 | 41 | 76 | 15 | 17 | 94 | 101 |
| Amine value (mgKOH/g) | 0 | 37 | 71 | 40 | 17 | 94 | 0 |
| Surface smoothness | 3 | 5 | 4 | 2 | 1 | 1 | 1 |

(Evaluation Method: Visibility and Identifiability from Blue Guide Wire)

The guide wires obtained from the Examples and the Comparative Examples were arranged on a blue drape for operating (trade name: Solution Pack, manufactured by Terumo Corporation), together with the a blue guide wire (trade name: Runthrough NS, manufactured by Terumo Corporation), and their visibility on the drape and their identifiability (distinguishability) from the blue guide wire were visually determined.

Compared to the blue guide wire, all of the guide wires of the Examples and the Comparative Examples showed higher visibility on the drape and excellent identifiability (distinguishability) from a blue guide wire.

From the above results, it was recognized that the guide wire obtained by using a dispersant which has an acid value of 20 to 90 mgKOH/g (Examples 1 to 3) has high visibility even on a blue non-woven fabric, and also has excellent identifiability from (i.e., is distinguishable from) the blue guide wire and high surface smoothness of a guide wire. On the other hand, the guide wire obtained by using a dispersant which has an acid value of less than 20 mgKOH/g, or more than 90 mgKOH/g (Comparative Examples 1 to 4) showed surface smoothness of a guide wire which is significantly lowered to the extent that it can be problematic in terms of actual use.

Example 4

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.05 g (relative to the titanium oxide: 0.10% by weight).

Example 5

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.08 g (relative to the titanium oxide: 0.16% by weight)

Example 6

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.10 g (relative to the titanium oxide: 0.20% by weight).

Example 7

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.20 g (relative to the titanium oxide: 0.40% by weight).

Example 8

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.26 g (relative to the titanium oxide: 0.52% by weight).

Example 9

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.29 g (relative to the titanium oxide: 0.58% by weight).

Example 10

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.35 g (relative to the titanium oxide: 0.70% by weight).

Example 11

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.5 g (relative to the titanium oxide: 1.00% by weight).

Example 12

A guide wire was obtained in the same manner as Example 2 except that, for preparing a coating solution for forming the first layer, the amount of ANTI-TERRA-204 (manufactured by BYK-Chemie, acid value: 41 mgKOH/g, amine value: 37 mgKOH/g) added as the dispersant A 0.31 g is modified to 0.60 g (relative to the titanium oxide: 1.20% by weight).

Surface smoothness of the guide wire was evaluated in the same manner as above. The results are shown in the following Table 2.

TABLE 2

| | Example 4 | Example 5 | Example 6 | Example 7 | Example 8 | Example 9 | Example 2 | Example 10 | Example 11 | Example 12 |
|---|---|---|---|---|---|---|---|---|---|---|
| Amount relative to the titanium oxide (wt %) | 0.10 | 0.16 | 0.20 | 0.40 | 0.52 | 0.58 | 0.62 | 0.70 | 1.00 | 1.20 |
| Surface smoothness | 3 | 4 | 4 | 5 | 5 | 5 | 5 | 5 | 4 | 3 |

The surface smoothness of the guide wire was high in virtually all of the Examples. In particular, with the added amount of the dispersant in Example 2 and Examples 5 to 11, the surface smoothness of the guide wire was high. Furthermore, the guide wire in all Examples showed higher visibility on a drape compared to the blue guide wire, and also exhibited excellent identifiability (distinguishability) from the blue guide wire.

Example 13

A guide wire was obtained in the same manner as Example 2 except that, for preparing a coating solution for forming the first layer, the amount of GARAMITE 7305 added as the thickening agent is modified from 1.0 g (relative to the solid content: 1.02% by weight) to 0.8 g (relative to the solid content: 0.82% by weight).

Example 14

A guide wire was obtained in the same manner as Example 2 except that, for preparing a coating solution for forming the first layer, the amount of GARAMITE 7305 added as the thickening agent is modified from 1.0 g (relative to the solid content: 1.02% by weight) to 1.8 g (relative to the solid content: 1.83% by weight).

Surface smoothness of the guide wire was evaluated in the same manner as above. The results are shown in the following Table 3.

TABLE 3

| | Example 13 | Example 2 | Example 14 |
|---|---|---|---|
| Amount relative to the solid content (wt %) | 0.82 | 1.02 | 1.83 |
| Surface smoothness | 5 | 5 | 5 |

The surface smoothness of the guide wire was high in each of the Examples 13-15. Furthermore, the guide wire in each of Examples 13-15 showed higher visibility on a drape compared to the blue guide wire, and also exhibited excellent identifiability (distinguishability) from the blue guide wire.

The detailed description above describes embodiments of a medical device and method for fabricating or producing a medical device representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device possessing a proximal-most end, the medical device comprising:
    an elongated body possessing a distal-most end, a proximal-most end and a distal portion extending from the distal-most end of the elongated body towards the proximal-most end of the elongated body;
    a first resin layer covering the proximal portion of the elongated body and not covering the distal portion of the elongated body, the first resin layer having a composition that includes a first fluororesin, titanium oxide, and a polymer dispersant that facilitates dispersion of the titanium oxide in the first fluororesin;
    a second resin layer covering the first resin layer and not covering the distal portion of the elongated body, the second resin layer having a composition that includes a second fluororesin;
    a content of the titanium oxide in the first resin layer is 30% by weight or more relative to a solid content of the first resin layer to color so that the proximal part of the medical device is colored, is visible against a colored fabric used in an operating room and is identifiable from other medical devices that are colored; and
    the polymer dispersant possessing an acid value that is 20 to 90 mgKOH/g and an amine value that is 30 mgKOH/g or more and 80 mgKOH/g or less to inhibit reduction of dispersion of the titanium oxide in the first fluororesin and improve surface smoothness of the proximal part of the medical device.

2. The medical device according to claim 1, wherein the first and second resin layers each possesses a distal-most end that is spaced proximally from the distal-most end of the elongated body by a distance of at least 300 mm.

3. The medical device according to claim 1, wherein the distal portion of the elongated body includes a first elongated portion, a second elongated portion and a third elongated portion, the first elongated portion possessing a distal-most end that is the distal-most end of the elongated body and also possessing a proximal-most end, the second elongated portion possessing a distal-most end directly connected to the proximal-most end of the first elongated portion and also possessing a proximal-most end, the third elongated portion possessing a distal-most end directly connected to the proximal-most end of the second elongated portion, the second elongated portion possessing a tapering shape that increases in outer diameter in a direction towards the proximal-most end of the second elongated portion, the third elongated portion possessing a constant outer diameter from the distal-most end of the third elongated portion towards the proximal-most end of the third elongated portion, the first and second resin layers each possessing a distal-most end spaced proximally from the proximal-most end of the second elongated portion of the distal portion of the elongated body.

4. The medical device according to claim 1, wherein a content of the polymer dispersant in the first resin layer is 0.10 to 3.00% by weight relative to the titanium oxide.

5. The medical device according to claim 4, wherein the polymer dispersant is a polyaminoamide-based dispersant.

6. The medical device according to claim 4, wherein the polymer dispersant is a polycarboxylic acid salt of polyaminoamide.

7. The medical device according to claim 1, wherein the first resin layer further includes a thickening agent.

8. The medical device according to claim 7, wherein an amount of the thickening agent is 0.50 to 3.00% by weight relative to the solid content of the first layer.

9. The medical device according to claim 1, wherein the first resin layer has a thickness of 0.8 to 100 µm.

10. The medical device according to claim 1, wherein the resin layer comprising the first resin layer and the second resin layer has a thickness of 1 to 200 µm.

11. The medical device according to claim 1, wherein a content of titanium oxide in the second resin layer is less than 5% by weight relative to the solid content of the second layer.

12. The medical device according to claim 1, wherein the medical device is a guide wire.

13. The medical device according to claim 12, wherein the first and second resin layers are located between a position that is spaced 300 mm from a distal end of the guide wire toward a proximal end side and a proximal end of the guide wire.

14. The medical device according to claim 12, wherein the first and second resin layers are located between a position that is spaced 300 mm from a distal end of the guide wire toward a proximal end side and a position that is spaced 3500 mm from the distal end of the guide wire toward the proximal end side.

15. The medical device according to claim 1, wherein a content of the titanium oxide in the first resin layer is 50% by weight or more and 75% by weight or less relative to a solid content of the first resin layer.

16. The medical device according to claim 1, wherein a content of the titanium oxide in the second resin layer is less than 1% by weight relative to the solid content of the second resin layer, and wherein the content of particles other than titanium oxide that are included in the second resin layer is less than 1% by weight relative to the solid content of the second resin layer.

17. The medical device according to claim 1, wherein the second resin layer substantially does not include any particles.

18. A medical device comprising:
an elongated body and a resin layer covering at least a proximal portion of the elongated body,
the resin layer comprising: i) a first layer which includes a first fluororesin, titanium oxide, and a dispersant; and ii) a second layer which is formed on the first layer and includes a second fluororesin,
a content of the titanium oxide is 30% by weight or more relative to solid content of the first layer, and
an acid value of the dispersant is 20 to 90 mgKOH/g and an amine value of the dispersant is 30 mgKOH/g or more and 80 mgKOH/g or less, and the dispersant improves surface smoothness of the proximal portion of the medical device.

19. The medical device according to claim 18, wherein the acid value of the dispersant is 40 to 85 mgKOH/g.

20. The medical device according to claim 18, wherein a content of the dispersant is 0.10 to 3.00% by weight relative to the titanium oxide.

21. The medical device according to claim 18, wherein the resin layer further includes a thickening agent.

22. The medical device according to claim 1, wherein the first fluororesin and the second fluororesin contain at least one selected from the group consisting of polytetrafluoroethylene (PTFE), tetrafluoroethylene-perfluoroalkyl vinyl ether copolymer (PFA), polychlorotrifluoroethylene (PCTFE), polyvinylidene fluoride (PVDF), polyvinyl fluoride (PVF), tetrafluoroethylene-hexafluoropropylene copolymer (FEP), and tetrafluoroethylene-ethylene copolymer (PETFE).

23. A method for producing a medical device comprising:
coating a first coating solution on at least a proximal portion of an elongated body to form a first coating film on the proximal portion of the elongated body, the first coating solution that is coated on the proximal portion of the elongated body to form the first coating film including a first fluororesin, titanium oxide, and a dispersant having an acid value of 20 to 90 mgKOH/g and an amine value of 30 mgKOH/g or more and 80 mgKOH/g or less to improve surface smoothness of the proximal portion of the medical device; and
coating a second coating solution on the first coating film to form a second coating film, the second coating solution that is coated on the first coating film to form the second coating film including a second fluororesin; and
baking the elongated body coated with the first and second coating films at a temperature which is equal to or higher than a melting point of the first fluororesin and a melting point of the second fluororesin.

* * * * *